United States Patent [19]

Hojo et al.

[11] 4,310,696

[45] Jan. 12, 1982

[54] PROCESS FOR PRODUCING INORGANIC ACID SALTS OF TERTIARY BUTYL HYDRAZINE

[75] Inventors: Shiro Hojo, Sakaide; Yoichi Hasegawa, Marukame; Mineo Nakagawa, Takamatsu, all of Japan

[73] Assignee: Japan Hydrazine Co., Inc., Tokyo, Japan

[21] Appl. No.: 164,229

[22] Filed: Jun. 30, 1980

[30] Foreign Application Priority Data

Jul. 5, 1979 [JP] Japan .................................. 54-85433

[51] Int. Cl.$^3$ .......................................... C07C 109/02
[52] U.S. Cl. .................................................. 564/464
[58] Field of Search ........................................ 564/464

[56] References Cited

U.S. PATENT DOCUMENTS

2,445,518  7/1948  Dreyfus ............................... 564/464
3,005,027 10/1961  Druey et al. ........................ 564/464
3,272,807  9/1966  Biel et al. ......................... 564/464 X

FOREIGN PATENT DOCUMENTS

880332 10/1961 United Kingdom ................ 564/464

OTHER PUBLICATIONS

Smith, "The Chemistry of Open–Chain Organic Nitrogen Compounds", vol. II, pp. 126 & 127, (1966).

Primary Examiner—John Doll
Attorney, Agent, or Firm—Armstrong, Nikaido, Marmelstein & Kubovcik

[57] ABSTRACT

Inorganic acid salts of tertiary butyl hydrazine such as hydrochloride or hydrobromide of tertiary butyl hydrazine, useful for production of azine compounds are substantially stoichiometrically produced by reaction of inorganic acid salts of hydrazine such as hydrochloride or hydrobromide of hydrazine with tertiary butyl halides such as chloride or bromide at a molar ratio of the tertiary butyl halides to inorganic acid salts of 1:7–10 at a reaction temperature of 90° to 110° C. for 40 to 100 minutes.

9 Claims, No Drawings

PROCESS FOR PRODUCING INORGANIC ACID SALTS OF TERTIARY BUTYL HYDRAZINE

This invention relates to a novel process for producing inorganic acid salts of tertiary butyl hydrazine by reaction of inorganic acid salts of hydrazine with tertiary butyl halides.

Inorganic acid salts of tertiary butyl hydrazine includes hydrochloride, hydrobromide, of tertiary butyl hydrazine, and is very useful as a raw material for producing azine compounds and other derivatives.

Heretofore, a process for producing a tertiary butyl hydrazine (which will be hereinafter referred to as "t-BH") by reaction of tertiary butyl urea, sodium hypochlorite and caustic soda is well known as Rasching process (U.S. Pat. Ser. No. 409,306, filed Nov. 5, 1964.) However, the process is not satisfactory for a commercial scale production due to such disadvantages that tertiary butyl urea is not always readily available at a low cost, the concentration of t-BH formed in the reaction product solution is low and the yield of t-BH is also as low as about 70%, and purification procedure is very complicated. It is also well known that alkyl hydrazines are formed by reaction of alkyl halides with hydrazine.

The present inventors have found that t-BH is not substantially formed by reaction of tertiary butyl halides (which will be hereinafter referred to as "t-BX") with hydrazine even under every conditions.

In view of an economy if t-BH can be synthesized from t-BH which is readily available at a low cost and hydrazine, and a great advantage obtained in the commercial production of t-BH, the present inventors have made extensive studies and have found that an inorganic acid salts of t-BH can be substantially stoichiometrically obtained by reaction of t-BX with inorganic acid salts of hydrazine, and have established the present invention.

In the present invention, appropriate inorganic acid salts of hydrazine include hydrazine hydrochloride, hydrazine hydrobromide, etc., but economically hydrazine hydrochloride is preferable. The inorganic acid salts of hydrazine are usually used as an aqueous 40-60% solution, and preferably as an approximately 50% aqueous solution.

Appropriate t-BX include tertiary butyl chloride (which will be hereinafter referred to as "t-BCl"), and tertiary butyl bromide, but t-BCl is preferable because of a lower cost.

A preferable molar ratio of t-BX to inorganic acid salt of hydrazine is in a range of 1:7-10.

Reaction temperature is usually 90° to 110° C., preferably 95° to 105° C.

Reaction time is preferably 40 to 100 minutes.

It is a surprising fact that, when the reaction is carried out under the afore-mentioned conditions, the reaction proceeds very readily and inorganic acid salts of t-BH can be substantially stoichiometrically obtained without any substantial formation of by-products. Anhydrous t-BH can be readily obtained by neutralization of the salts and successive distillation or extraction.

The present process can be carried out even batchwise, but it is preferable to recycle the reaction solution.

The present process, when t-BCl and hydrazine hydrochloride (which will be hereinafter referred to as "H.HCl") are used as the raw materials and the reaction solution is recycled, will be described below.

That is, n moles of H.HCl and a moles of t-BCl are allowed to react. After completion of the reaction, the reaction solution is cooled to about 10° C., whereby t-BH hydrochloride (which will be hereinafter referred to as "t-BH.HCl") will be deposited as crystal. The t-BH.HCl crystal is separated, and the mother liquor is returned to the reactor. Then, a mole of hydrazine (which will be hereinafter referred to as "H"), which is in equal moles to the moles of previously charged t-BCl, and a moles of t-BCl are charged, whereby H will be converted to H.HCl by hydrochloric acid formed by the reaction. Thus, the reaction of H.HCl with t-BCl can be repeated. The foregoing relations can be summarized below:

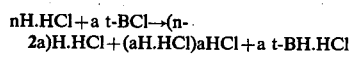

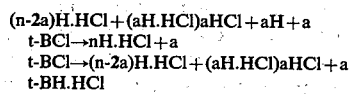

The separated crystal of t-BH.HCl is washed with a small amount of water, and then neutralized with aqueous solution of caustic soda, and tertiary butyl hydrazine can be obtained by distilling the above neutralized solution. When t BH is allowed to react with ketones directly, azine compounds can be readily obtained. The azine compounds are very useful as raw materials for azobis compounds, or a polymerization initiator.

The present invention will be described in detail below, referring to Examples.

EXAMPLE 1

120.5 g (0.88 moles) of an aqueous 50% solution of H.HCl and 9.25 g (0.1 mole) of t-BCl were charged into a glass autoclave and subjected to reaction at a temperature of 100° to 105° C. for 60 minutes. The resulting reaction product solution was analyzed by gas chromatography, and it was found that a yield of t-BH on the basis of t-BCl was 99.9%. The reaction product solution was cooled to 10° C., and deposited crystal of t-BH.HCl was recovered and washed with a very small amount of water, and dried. Then, HCl content was measured. It was found 29.12% (calculated: 29.29%). Its melting point was 190°–191° C. (literature value: 192° C.).

EXAMPLE 2

Reaction product mother liquor was cyclically subjected to reaction in a 50-l, glass-lined reactor.

First reaction was carried out by charging 21.9 kg (0.16 k-moles) of an aqueous 50% solution of H.HCl and 1.85 kg (0.02 k-moles) of t-BCl into the reactor, and heating to 100°–105° C. with stirring. Reaction pressure was initially increased to 4 kg/cm² gage, but decreased to 0.7 kg/cm² gage after 40 minutes. Stirring was further continued for 20 minutes and then the reaction product solution was cooled to 10° C. Deposited crystal of t-BH.HCl was separated and its weight and content were measured. The mother liquor was charged into the reactor for successive reaction, and 1.0 kg (0.02 k-moles) of H was charged thereto. Successive reaction was carried out in the same manner as in the first reaction. Results are shown in Table.

TABLE

| Reaction | Charged (kg) | | | | Reaction product solution | | | |
| --- | --- | --- | --- | --- | --- | --- | --- | --- |
| | Mother liquor | *H | t-BCl | Reaction solution | Crude t-BH.HCl | Pure t-BH.HCl | Yield (%) | Mother liquor |
| 1st | 21.9 | 0 | 1.85 | 23.75 | 1.526 | 1.35 | 54.2 | 22.2 |
| 2nd | 22.2 | 1 | 1.85 | 25.05 | 2.643 | 2.36 | 94.8 | 22.38 |
| 3rd | 22.38 | 1 | 1.85 | 25.23 | 2.77 | 2.45 | 98.43 | 22.44 |
| 4th | 22.44 | 1 | 1.85 | 25.29 | 2.904 | 2.57 | 103.25 | 22.37 |
| 5th | 22.37 | 1 | 1.85 | 25.22 | 2.958 | 2.63 | 105.65 | 22.39 |
| 6th | 22.31 | 1 | 1.85 | 25.16 | 2.97 | 2.62 | 105.26 | 22.17** |
| Total | | | 11.1 | | 13.98 | | 99.77 | 0.93 |

\* H: 100% $NH_2NH_2H_2O$
\*\* It was found by analysis that mother liquor contained 0.93 kg of t-BH . HCl.

It is obvious from Table that pure t-BH.HCl amounts to total 14.91 kg including 0.93 kg of 6th reaction mother liquor (calculated: 14.93 kg) and a yield is 99.77%.

What is claimed is:

1. A process for producing inorganic acid salts of tertiary butyl hydrazine, which comprises reacting inorganic acid salts of hydrazine with tertiary butyl halides, thereby producing the inorganic acid salts of tertiary butyl hydrazine.

2. A process according to claim 1, wherein the inorganic acid salt of tertiary butyl hydrazine is hydrochloride or hydrobromide of tertiary butyl hydrazine.

3. A process according to claim 1, wherein the inorganic acid salt of hydrazine is hydrochloride or hydrobromide of hydrazine.

4. A process according to claim 1 or 3 wherein the inorganic acid salt of hydrazine is used as an aqueous 40–60% solution.

5. A process according to claim 1, wherein the tertiary butyl halide is tertiary butyl chloride or tertiary butyl bromide.

6. A process according to claim 1, wherein a molar ratio of the tertiary butyl halides to the inorganic acid salts of hydrazine is 1:7–10.

7. A process according to claim 1, wherein the reaction is carried out at 90° to 110° C. for 40 to 100 minutes.

8. A process according to claim 1, wherein the resulting inorganic acid salt of tertiary butyl hydrazine is separated as crystal from the resulting product solution, and neutralized and the resulting solution is allowed to distillation, thereby obtaining anhydrous tertiary butyl hydrazine.

9. A process according to claim 1, wherein the resulting inorganic acid salt of t-BH is separated as crystal from resulting product solution, and the mother liquor is cyclically subjected to the reaction.

* * * * *